Figure 1:
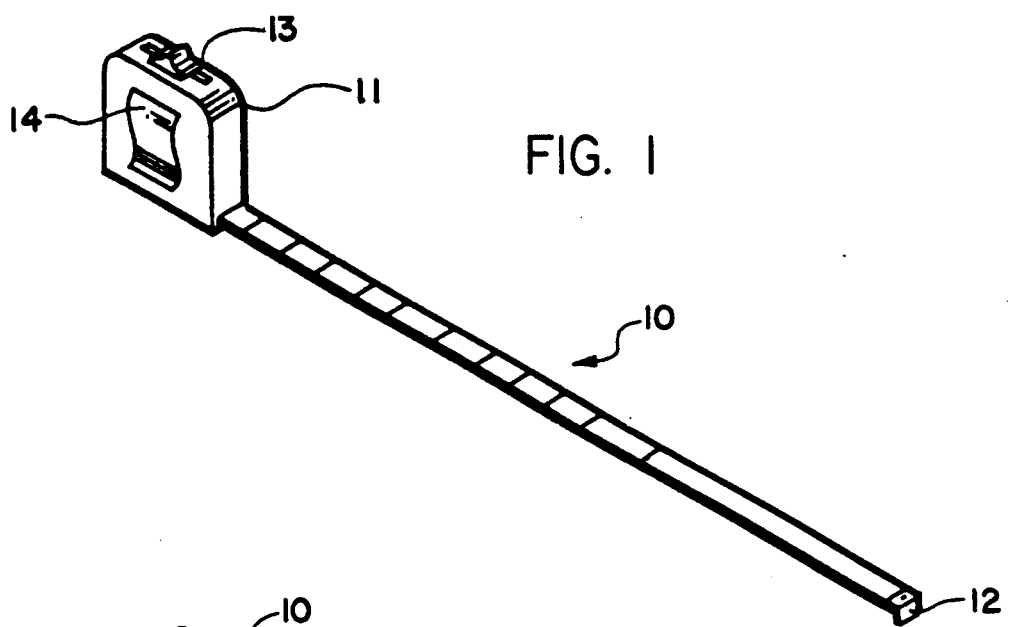

United States Patent [19]

Broselow

[11] Patent Number: 5,010,656

[45] Date of Patent: Apr. 30, 1991

[54] THERAPEUTIC APPARATUS

[76] Inventor: James B. Broselow, 24 White Eagle Ranch, Rte. 12, Hickory, N.C. 28602

[21] Appl. No.: 595,657

[22] Filed: Oct. 9, 1990

Related U.S. Application Data

[63] Continuation of Ser. No. 197,592, May 23, 1988, abandoned, which is a continuation-in-part of Ser. No. 133,956, Dec. 17, 1987, Pat. No. 4,823,469, which is a continuation-in-part of Ser. No. 910,490, Sep. 23, 1986, Pat. No. 4,713,888, which is a continuation-in-part of Ser. No. 789,497, Oct. 21, 1985, abandoned.

[51] Int. Cl.$^5$ .............................................. G01B 3/02
[52] U.S. Cl. .................................... 33/759; 33/760; 33/512
[58] Field of Search ................ 33/755, 756, 758, 759, 33/494, 483, 511, 512, 515; 235/86, 87 A, 7 A; 128/630, 774; 604/189; 5/508; 283/900; 434/262; 116/308; 141/22, 23, 24; 73/426, 427; 215/11.1, DIG. 3; 220/500

[56] References Cited

U.S. PATENT DOCUMENTS

| | | | |
|---|---|---|---|
| 1,507,968 | 9/1924 | Johnson | 73/427 |
| 1,624,779 | 4/1927 | De Camp et al. | |
| 2,932,897 | 4/1960 | Huber | 33/758 |
| 3,020,643 | 2/1962 | Moran | 33/138 |
| 3,196,551 | 7/1965 | Provost et al. | 33/174 |
| 3,336,674 | 8/1967 | Higgins et al. | 33/138 |
| 3,520,293 | 7/1970 | Atherholt | 128/2 |
| 3,531,866 | 10/1970 | Lawler et al. | 33/143 |
| 3,645,262 | 2/1972 | Harrigan | 215/11.1 |
| 3,931,741 | 1/1976 | Ceccarelli | 73/427 |
| 4,079,629 | 3/1978 | Hope | 73/427 |
| 4,192,360 | 3/1980 | Rodriquez | 141/24 |
| 4,345,541 | 8/1982 | Villa-Real | 116/308 |
| 4,347,804 | 9/1982 | Villa-Real | 116/308 |
| 4,366,623 | 1/1983 | Bergqvist | 33/140 |
| 4,416,381 | 11/1983 | Swartwout | 73/427 |
| 4,713,888 | 12/1987 | Broselow | 33/759 |
| 4,817,808 | 4/1989 | Bracy | 220/20 |

FOREIGN PATENT DOCUMENTS

| | | |
|---|---|---|
| 411334 | 6/1910 | France . |
| 423343 | 4/1911 | France . |
| 1453008 | 8/1966 | France . |
| 2507767 | 12/1982 | France . |
| 5060 | of 1894 | United Kingdom . |
| 812717 | 4/1959 | United Kingdom . |
| 937006 | 9/1963 | United Kingdom . |

Primary Examiner—William A. Cuchlinski, Jr.
Assistant Examiner—C. W. Fulton
Attorney, Agent, or Firm—W. Thad Adams, III

[57] ABSTRACT

An apparatus for therapeutic treatment of a patient. A measuring tape is used to measure the heel-to-crown height of a patient. The tape has coded zones along its effective length. A dispenser is provided with correspondingly coded zones whereby a treatment administered using the coding of the dispenser is correlated to the heel-to-crown height of a patient as measured by the tape.

10 Claims, 2 Drawing Sheets

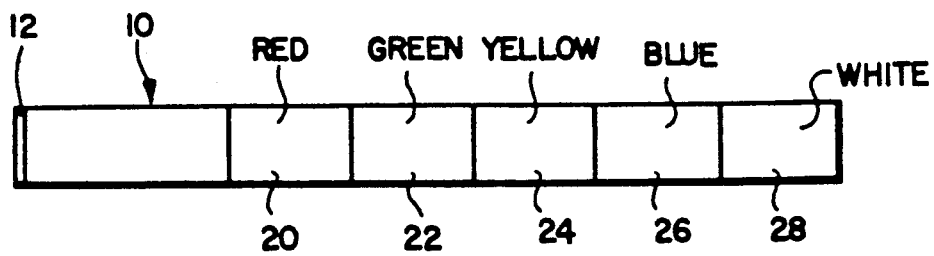
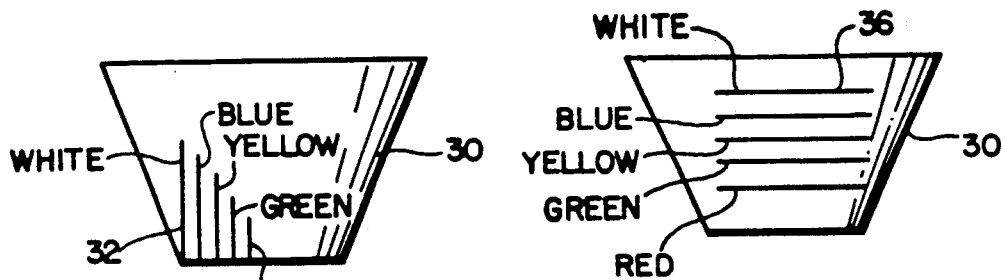
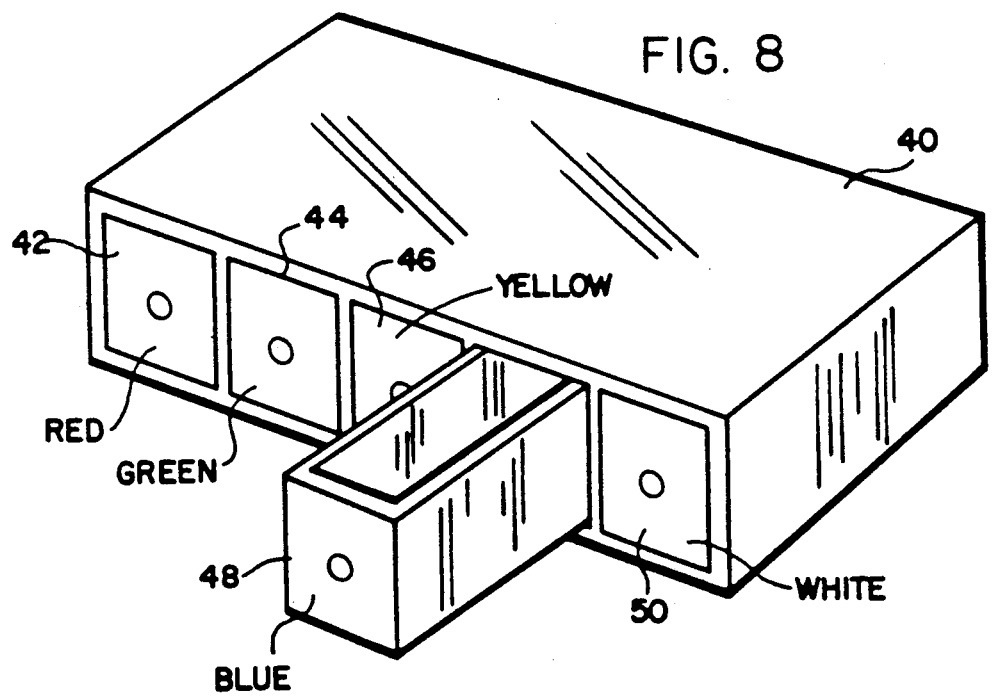
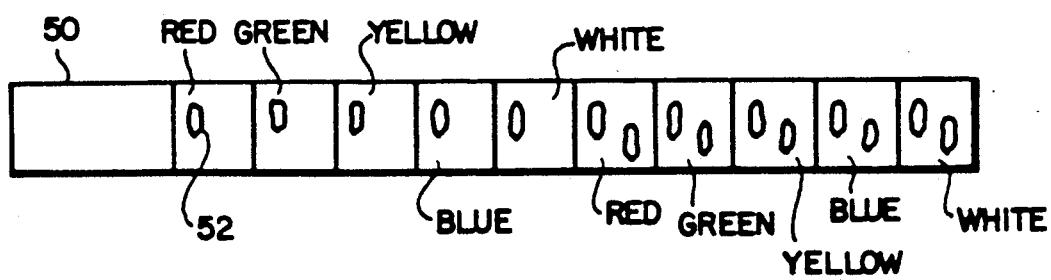

THERAPEUTIC APPARATUS

This application is a continuation of appliaction Ser. No. 197,592, now abandoned, filed May 23, 1988, which is a C-I-P of U.S. Ser. No. 133,956, filed Dec. 17, 1987 now issued as U.S. Pat. No. 4,823,469 on Aug. 25, 1989, which is a C-I-P of U.S. Ser. No. 910,490, filed Sept. 23, 1986, now issued as U.S. Pat. No. 4,713,888 on Dec. 22, 1987, which is a C-I-P of U.S. Ser. No. 789,497, filed Oct. 21, 1985, now abandoned.

This invention relates to therapeutic apparatus which can be used in situations where it is necessary to determined with accuracy a variable of the treatment.

Perhaps tha most obvious variable is that of drug dosage. It is guite usual for drug dosage to be determined by the age of the patient (particularly if the patient is an infant or child) but this is a very inaccurate method and would be totally inappropriate in the adminstration of toxic drugs, for instance in chemotherapy. Beside, the age of the patient is not always readily determinable in emergencies or in situations where language and/or illiteracy may be a problem.

In medical practice, drug dosages have been baced historically on the body weight of the patient. The physician must therefore first estimate the weight of the patient (it is not always practicable to weight the patient especially in emergencies), the either consult tables to determine the appropriate dosage, or determine the dosage by memory, and then multiply that dosage by the estimated weight. The possibility of error is present and is increased by the pressure of time and circumstances which often attend emergency medical treatment. On the other hand, as medical treatment has become more complex, drug dosages have become more critical, and therefore errors could have very dangerous, and even lethal results.

Another example of a therapeutic treatment variable is the tube size of an endotracheel tube, which has to be introduced through the epiglottis of the patient. On the one hand the tube must not be too large, or it will damage the throat tissues, and on the other hand, if it is too small, it will leave a clearance which could vitiate the treatment entirely. Clearly the correct tube size is related to the size of the patient. Another patient-size related variable is that of tube length in the case of an endotracheal tube.

It will be appreciated therefore that in therapeutic treatment, there is a range of variables measurable in physical quantities or dimensions, and it is a fact that estimating the weight of the patient is the most commonly used method of assessing the variables.

However, it has been recognised that in many cases, weight is an inaccurate and inappropriate basis on which to determine physical treatment values such as drug dosages, tube lengths and sizes, medical equipment settings and like patient-related treatment and apparatus. Despite this, weight remains the most commonly practiced way of determining these values. In many cases, length is a much more appropriate way to determine many physical treatment values. For example, the length of an endotracheal tube is very closely related to the overall length of a patient, whether that patient is underweight, overweight or of an ideal weight. Likewise, it is now known that an obese patient weighing significantly more than a patient of normal weight will certainly not need an increase in the dosage of most drugs proportional to his weight and, in fact, can be dosed to toxic levels in this way. This is because many drugs distribute only in the lean body tissue.

The present invention provides apparatus enabling accurate and swift determination of a correct therapeutic treatment to be administered, which is based on the length of the patient.

According to this invention, apparatus for therapeutic treatment of a patient comprises a measuring tape for measuring the heel to crown heighf of a patient and a dispenser (as herein defined) and is characterised in that the measuring tape is divided along its effective length into coded zones and the dispenser is divided into correspondingly coded zones whereby a treatment obtained by using the coding of the dispenser is related to the heel to crown height of a patient as measured by the tape.

The background to the inventon has been explained with reference to medical practice, but it is to be understood that it is equally applicable to veterinary paractice and therefore the term "patient" is to be construed as including anlmals as well as humans. For simplicity however, the specific examples quoted herein relate to the treatment of humans.

Also the term "dispenser" is to be broadly construed. A very simple dispenser may comprise a cup or spoon for administering liquids orally; a more sophisticated dispenser is a droplet type dispenser which can be used to administer very small and critical quantities of drugs, and another form of dispenser comprises a series of compartments, each containing one or more items of apparatus (e.g. endotracheal tubes).

A simple and very effective coding is provided by colour coding, but other codes such as cross hatching; lettering; numbering or illustrations of one or a plurality of dispensers or any combination of these methods of coding may be employed.

To take simple illustration, the measuring tape may be divided into differently coloured increments of length (e.g. red; green, yellow; blue; white) and a cup type medicine dispenser for use with the tape marked with levels shown as red; green; yellow; blue; white. Therefore, by simply measuring the patient and filling the dispenser to the colour level corresponding to the colour on the tape read off from the patient's height, it is ensured the medicine dose is co-related to the height of the patient. However, quite critical drug dosages can also be dispensed by the same method using a more sophisticated, but similarly coded dispenser.

Taking another illustration, in a hospital emergency or casualty ward, the dispenser may comprise a set of containers (e.g. drawers) each containing a set of apparatus likely to be needed in emergency treatment, but with different sizes of some or all of the items in each container. When a patient is to receive treatment the appropriate colour code is read off by measuring the patient's height and then the container of that colour is selected. The physician is then presented with a set of apparatus all of the correct sizes appropriate to the patient's length.

Obvious advantages of the invention are that the selection of the correct variable can be made very quickly, (since it is only necessary to measure the patient's length) and that the selection can be made by a relatively untrained staff, certainly by illiterate personnel (or personnel illiterate in the language of any printed instructions) and without any calculations. The possibility of error is greatly reduced and the variable selected according to heel to crown height which is usually a more useful guide than estimated body weigth.

Figure 2:
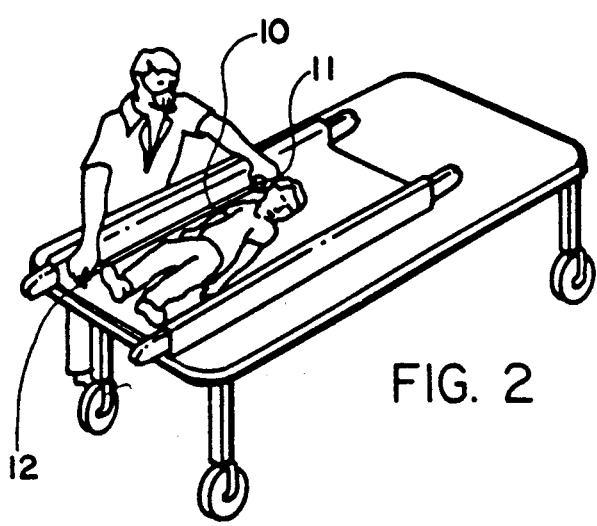
Figure 3:
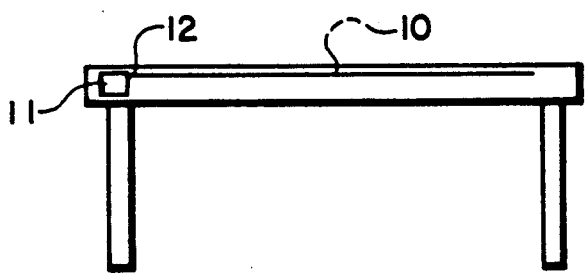
Figure 4:
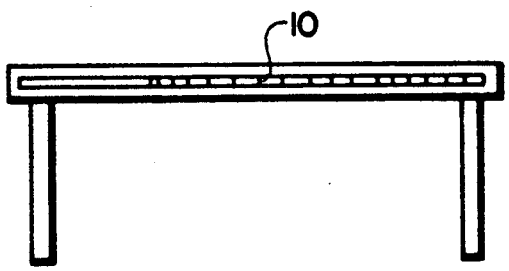

The invention will be more clearly understood from thre following description of certain specific embodiments of the invention which are described by way of examples only, and with reference to the accompanying drawings in which;

FIG. 1 is a perspective view of one embodiment of a measuring tape according to the present invention, FIG. 2 is a perspective view illustrating the manner of using the measuring tape illustrated in FIG. 1, FIG 3 is a side elevational view of the measuring tape mounted for use on the side of a stretcher, FIG. 4 is a side elevational view of the measuring tape affixed to the side of a stretcher in an extended form, FIG. 5 is a plan view of the measuring tap in accordance with this embodiment, FIG. 6 is an elevational view of the cup type dispenser for liquids, FIG. 7 is a view similar to FIG. 6, but showing a diffferent method of coding a cup type dispenser, FIG. 8 is a perspective view of a drawer type dispenser, and FIG. 9 is a plan view of an alternative form of measuring tape showing another method of coding.

A measuring tape according to a first embodiment of the invention is shown in FIG. 1, and indicated by the reference number 10. The tape 10 can be constructed with various differing physical characteristics. Perferably, it comprises a steel type tape having a cupped cross section which provides increased rigidity to the tape and at the same time allows flexibility when needed. According to the embodiment shown in FIG. 1, the tape is retractably mounted inside an enclosure 11. One end of the tape is connected to a spring return mechanism (not shown) located within the enclosure 11. The tape is used by withdrawing it from the enclosure 11 by means of a pull tab 12 at the free end of the tape. To retract the end of the tape, a button 13 on the enclosure 11 is pressed, and this causes the tape 10 to retract into the enclosure 11. A belt clip 14 is provided on one side of the enclosure 11 so that the enclosure can be secured to the user's belt or to a pocket.

Turning now to FIG. 5, there is illustrated the manner in which the measuring tape 10 is divided into a series of length increments 20, 22, 24, 26 and 28. FIG. 5 also illustrates how these length increments are colour coded, that is to say each increment of the measuring tape has a distinctive colour, in this case, the colour coding being as follows:

| 20 | Red |
| 22 | Green |
| 24 | Yellow |
| 26 | Blue |
| 28 | White |

The colour coded length measurements are so arranged, that if the tape is used to measure the heel to crown height of a patient, that measured height which will be read off as a colour code, will in fact be co-related to the ideal or lean body weigth of the patient, although the tape itself will give no direct weight neasurement. Therefore, the measuring tape 10 automatically takes into account that for example, drug dosage does not increase in direct proportion to an increase in weight of the patient. This is desirable, since most emergency drug dosages are based on "lean" body weight, because drugs do not distributs into fatty tissue at the same rate or to the same extent as into organ and muscle tissue during the time frame of emergency treatment.

In FIG. 6, there is illustrated a simple transparent plastics cup 30, which can be used for the administration of medicines to a patient. It will be observed, that a series of vertical lines 32 is provided on the wall of the cup 30, and these lines may in fact be etched into the wall of the cup. Moreover, the vertical lines 32 are of differing lengths, and are colour coded, to the same as those used for the length increments on the measuring tape 10. The arrangement of the vertical lines 32, is such that for a given type of medicine, a correct dose for a patient having a height measured into the red increment 20 on the tape 10, would be given by filling the cup 30 to the top of the red vertical line.

Similarly, a correct dosage of the medicine would be administered to a patient measured into say the blue zone of the measuring tape 10, by filling the cup 20 up to the top of the blue vertical line.

It will be appreciated therefore, that there is a direct co-relation between the measured heel to crown height of the patient, and the medicine which is administered. This co-relation is obtained without any calculation, and without the necessity for the reading off of numerical values on the measuring tape. Moreover, it is not necessary for the person administering the medicine to be literate since no instructions have to be read, Hence, the apparatus comprising the measuring tape 10 and the dispensing cup 30 can be used in situations where it is not practicable to have medically trained supervision. For instance, in areas remote from medical personnel, untrained people, such as the parent of a child, with be able to give the correct dosage of a medicine over a length of time during which the child will be growing, by simply measuring the height of the child using the tape 10, and then selecting the appropriate fill of the cup as given by the corresponding colour coding on the cup.

In FIG. 7, there is illustrated a cup 34 which is very similar to the cup 30 illustrated in FIG. 6, excepting that the vertical colour coded lines 32 are replaced by horizontal colour coded lines 36.

Some medicines and drugs are administered by more sophisticated dispensers such as droplet dispensers, or hyperdermic needles. However, it will be appreciated that these more sophisticated types of dispenser could have colour coding applied thereto corresponding to the colour coding of a measuring tape of the kind illustrated at 10. For instance, where the drug is pre-packed in dispensers of differing sizes, the different sizes of dispenser could be colour coded in accordance with the colour code on the measuring tape. Alternatively where the dispenser has a transparent zone through which the drug can be observed, there may be a colour coding on the transparent zone which will enable the person administering the drug to use a quantity dictated in accordance with the colour coding. Therefore, even in quite sophisticated medical practice, the tape measure 10 can be used in association with a correspondingly colour coded dispenser or set of dispensers in order to give a dosage which is related to the height of the patient, and thereby indirectly related to the ideal weight of the patient.

Turning now to FIG. 8, there is illustrated a dispenser, which is intended to be used in an emergency or casualty ward of a hospital, and which in effect comprises a container 40 comprising a series of drawers 42; 44; 46; 48 and 50. FIG. 8 illustrates how the fronts of these drawers are coloured according to a similar colour coding scheme as that applied to the measuring tape 10, that is to say the drawer 42 is coloured red, the drawer 44 is coloured green and so on.

In use, each of these drawers 42 to 50 contains either a single piece of medical or surgical apparatus, such as an endotracheal tube, or it may contain a kit of items of apparatus, including pre packed drugs. The significance of the arrangement is that each drawer contains an apparatus or kit pieces of apparatus, which are of the correct values in terms of dosage or size, for the treatment of a patient the height of which has been read off according to the colour coding on the measuring tape 10.

One of the problems of an emergency or casualty ward, is that treatment generally has to be initiated under pressure. On the other hand, the size of certain pieces of equipment, for instance the diameter of an endotracheal tube can be quite critical to the success of the treatment which is some cases may be vital. However, by simply measuring the heel to crown height of the patient, reading off the appropriate colour coding, and then selecting the correspondingly colour code drawer, it is ensured that the apparatus which is used is correct for the patient having that height. Again therefore, it will be appreciated that there is a great saving in time and stress on the staff in the emergency situation, and some guarantee that the correct treatment will be applied.

In some instances, simple colour coding by itself may not be sufficient, since obviously it is best if the colour coding can rely on only primary colours, and more than a few length increments may be needed. FIG. 9 illustrates an alternative measuring tape 50 having a series of ten length increment zones. It will be observed from FIG. 9 that the zones are coloured in the sequence; red; green; yellow; blue; white; red; green; yellow; blue; white. However, the first five zones each bear the representation (diagrammatic) of a single dispenser 52, whereas the second set of five zones each has the representation of two dispensers. This is intended to indicate to a user, that if the measured length of a patient is in the second set of five colour coded zones, the appropriate dosage will be twice that which will be given if the measured length were in one of the first five colour coded zones. This therefore illustrates a method whereby the colour coding may be supplemented by an additional coding method to increase the number of length increments which are available on the measuring tape. It will be appreciated, that colour coding is not the only method by which the dispenser could be coded, for instance letter or symbol coding could be employed.

Referring back now to FIG. 2, the tape 10 or 50, can be used as a conventional measuring tape. That is, the enclosure 11 is placed at one end of the patient and the measuring tape 10 is extended so that the pull tab 12 of the measuring tape is at the other end of the patient. Then the coding is read directly off the tape 10 as previously described.

As is shown in FIG. 3, the enclosure 11 can be mounted at the head or foot end of a stretcher. When a patient is placed on a stretcher, a measurement can be taken by extending the measuring tape 10 along the length of the stretcher to the other end of the patient's body. Another variation of the invention is shown in FIG. 4, where a measuring tape 10 is fixed along the length of a stretcher, so that a reading can be taken directly without manipulating the tape at all. It is only necessary to make sure that one of the patient's body is adjacent to one end of the tape.

The tape 10 has been described above with reference to total heel to crown body length. However, it will be approciated, that the tape can also be used with any body part length or body subsegment length to which a desired treatment value can be co-related.

I claim:

1. Apparatus for selection of emergency medical equipment and drug dosages for therapeutic treatment of a patient comprising:
   (a) a measuring tape for measuring the heel-to-crown height of a patient, said measuring tape having coded zones representing a medical equipment of drug dosage indication along an effective length thereof; and
   (b) a treatment dispenser having a plurality of sections containing emergency medical equipment and drugs, said dispenser sections being correspondingly coded to the measuring tape whereby a treatment administered using the coding of the treatment dispenser is correlated to the heel-to-crown height of a patient as measured by the tape.

2. Apparatus for treatment of a patient according to claim 1, wherein said dispenser comprises a receptacle for administering drugs orally.

3. Apparatus for treatment of a patient according to claim 1, wherein said dispenser comprises a droplet-type dispenser which can be used to administer very small and critical quantities of drugs.

4. Apparatus for treatment of a patient according to claim 1, wherein said dispenser comprises a series of compartments, each compartment adapted to contain at least one item of medical equipment.

5. Apparatus for treatment of a patient according to claim 1, wherein said measuring tape and dispenser are each color coded, said color coding of each of said measuring tape and dispenser mutually correlated to the other.

6. Apparatus for therapeutic treatment of a patient comprising:
   (a) a measuring tape for measuring the heel-to-crown height of a patient, said measuring tape having coded zones along an effective length thereof; and
   (b) a treatment dispenser, said treatment dispenser having correspondingly coded zones whereby a treatment administered using the coding of the dispenser is correlated to the heel-to-crown height of a patient as measured by the tape.

7. Apparatus for therapeutic treatment of a patient according to claim 6, wherein said dispenser comprises a receptacle for administering drugs orally.

8. Apparatus for treatment of a patient according to claim 6, wherein said dispenser comprises a droplet-type dispenser which can be used to administer very small and critical quantities of drugs.

9. Apparatus for treatment of a patient according to claim 6, wherein said dispenser a series of compartments, each compartment adapted to contain at least one item of medical equipment.

10. Apparatus for treatment of a patient according to claim 6, wherin said measuring tape and dispenser are each color coded, said color coding of each of said measuring tape and dispenser mutually correlated to the other.

* * * * *